United States Patent
Nishiyama et al.

(10) Patent No.: US 8,030,622 B2
(45) Date of Patent: *Oct. 4, 2011

(54) SPECIMEN HOLDER, SPECIMEN INSPECTION APPARATUS, AND SPECIMEN INSPECTION METHOD

(75) Inventors: Hidetoshi Nishiyama, Tokyo (JP); Mitsuru Koizumi, Tokyo (JP); Mitsuo Suga, Saitama (JP)

(73) Assignee: JEOL Ltd., Tokyo (JP)

( * ) Notice: Subject to any disclaimer, the term of this patent is extended or adjusted under 35 U.S.C. 154(b) by 228 days.

This patent is subject to a terminal disclaimer.

(21) Appl. No.: 12/478,111

(22) Filed: Jun. 4, 2009

(65) Prior Publication Data

US 2009/0314955 A1    Dec. 24, 2009

(30) Foreign Application Priority Data

Jun. 20, 2008    (JP) ................................ 2008-161476

(51) Int. Cl.
*H01J 37/20* (2006.01)
*G01N 1/28* (2006.01)
*G21K 5/08* (2006.01)

(52) U.S. Cl. .............. 250/440.11; 250/442.11; 250/306; 250/310; 250/311; 250/309; 73/864.91

(58) Field of Classification Search ............. 250/440.11, 250/442.11, 306, 310, 311, 309; 73/864.91
See application file for complete search history.

(56) References Cited

U.S. PATENT DOCUMENTS

| | | | |
|---|---|---|---|
| 4,990,776 A * | 2/1991 | Fushimi et al. | 250/310 |
| 7,745,802 B2 * | 6/2010 | Nishiyama et al. | 250/442.11 |
| 2009/0250609 A1 * | 10/2009 | Nishiyama et al. | 250/306 |
| 2010/0019146 A1 * | 1/2010 | Nishiyama et al. | 250/307 |
| 2010/0243888 A1 * | 9/2010 | Nishiyama et al. | 250/307 |

FOREIGN PATENT DOCUMENTS

| | | |
|---|---|---|
| JP | A-47-24961 | 10/1972 |
| JP | A-51-42461 | 4/1976 |
| JP | A-6-318445 | 11/1994 |
| JP | T-2004-515049 | 5/2004 |

OTHER PUBLICATIONS

Green, Evan Drake Harriman, Ph.D., "Atmospheric Scanning Electron Microscopy," Chapter 1: Introduction, Stanford University, 1993, pp. 1-12.

* cited by examiner

*Primary Examiner* — Nikita Wells
(74) *Attorney, Agent, or Firm* — The Webb Law Firm

(57) ABSTRACT

A specimen holder is offered which can reduce the amount of chemical sprayed over a specimen consisting of cultured cells. The specimen holder has an open specimen-holding surface. At least a part of the specimen-holding surface is formed by a film and a tapering portion formed around the film. The specimen can be cultured on the specimen-holding surface of the film. The presence of the tapering portion can reduce the amount of used reagent. The specimen can be irradiated via the film with a primary beam for observation or inspection of the specimen. Consequently, the specimen, such as cells, can be well observed or inspected in vivo while the specimen is being cultured. Especially, if an electron beam is used as the primary beam, the specimen can be well observed or inspected in vivo by SEM (scanning electron microscopy).

19 Claims, 4 Drawing Sheets

SPECIMEN HOLDER, SPECIMEN INSPECTION APPARATUS, AND SPECIMEN INSPECTION METHOD

BACKGROUND OF THE INVENTION

1. Field of the Invention

The present invention relates to a specimen holder, specimen inspection apparatus, and specimen inspection method capable of observing or inspecting a specimen consisting of cultured tissues and cells of an animal or plant.

2. Description of Related Art

In the fields of life science and pharmaceutics, it has become important to observe reactions of biological cells produced by giving a stimulus (such as electricity, chemical substance, or medicine) to them. In the past, optical microscopes have been used for such observation. Manipulators or pipettes have been employed to give stimuli to cells. Frequently, important portions to be observed are very tiny regions of less than 0.1 μm that are impossible to observe with an optical microscope.

For example, diseases arising from the inability to exchange substances normally among biological cells include hypertension, diabetes insipidus, arrhythmia, myopathy, diabetes, and deprementia. Exchange of substances among cells is performed by ion channels having sizes of about 10 nm and existing in cell membranes. Because it is difficult to observe such ion channels with optical microscopes, there has been a demand for a technique enabling observation using a scanning electron microscope (SEM) having high resolution.

However, a specimen to be inspected with an inspection apparatus incorporating SEM capabilities is normally placed in a specimen chamber whose internal pressure has been reduced by vacuum pumping. The specimen placed in the specimen chamber, which, in turn, is placed in a reduced-pressure ambient in this way, is irradiated with an electron beam (charged-particle beam). Secondary signals, such as secondary electrons or backscattered electrons, produced from the specimen in response to the irradiation are detected.

In such inspection of a specimen using SEM, the specimen is exposed to a reduced-pressure ambient. Therefore, moisture evaporates from the specimen, so that the cells die whereupon it has been impossible to observe reactions of living cells to a stimulus.

When a specimen consisting of dead cells where the proteins have been fixed is placed in a reduced-pressure ambient or vacuum ambient, much labor and various pretreatments, such as dehydration, drying, and metal vapor deposition, that require a high degree of skillfulness have been necessary to prevent evaporation of moisture within a vacuum; otherwise, the specimen would be deformed. Accordingly, an excessively long time has been required to observe the specimen. It has not been possible to achieve high throughput observations.

For these reasons, in order to observe a biological specimen, it is desired to prevent evaporation of moisture. When an inspection is performed under the condition where the specimen contains moisture, it is necessary to prevent the specimen from being exposed to the reduced-pressure ambient; otherwise, moisture would evaporate from the specimen. One conceivable method of inspecting a specimen using SEM without exposing the specimen to a reduced-pressure ambient in this way consists of preparing a specimen holder (sample capsule) whose opening (aperture) has been sealed off by a film, placing the specimen in the holder, and installing the holder in an SEM specimen chamber that is placed in the reduced-pressure ambient.

The inside of the specimen holder in which the specimen is placed is not evacuated. The film that covers the opening formed in the sample capsule withstands the pressure difference between the reduced-pressure ambient inside the SEM specimen chamber and the ambient (e.g., atmospheric-pressure ambient) of the inside of the specimen holder that is not pumped down. Furthermore, the film permits an electron beam to pass therethrough (see JP-T-2004-515049).

When a specimen is inspected, an electron beam is directed at the specimen placed within the sample capsule from outside the capsule via the film on the capsule. The capsule is placed in the SEM specimen chamber at a reduced-pressure ambient. Backscattered electrons are produced from the irradiated specimen. The backscattered electrons pass through the film on the capsule and are detected by a backscattered electron detector mounted in the SEM specimen chamber. Consequently, an SEM image is derived.

However, with this technique, the specimen is sealed in the closed space and thus it has been impossible to give a stimulus to cells from the outside with a manipulator or the like. Where the cells should be observed or inspected in vivo for a long time after the specimen consisting of the cells has been sealed in the sample capsule, there arises a problem.

Furthermore, an SEM image has high resolution but contains only black-and-white information. Therefore, it has been difficult to identify the observed tissue. On the other hand, in optical microscopy, fluorescence labeling technology has been established, and it is easy to identify tissues. If an SEM image and an optical microscope image derived from a substantially identical position can be observed substantially at the same time, the tissues can be identified with the high-resolution SEM image. However, with the aforementioned sample capsule, it is necessary to open the capsule for obtaining an optical microscope image. In order to derive an SEM image, it is necessary to close the capsule. Hence, it has been impossible to achieve the simultaneous observation.

Usually, cells are cultured by adsorbing them onto a laboratory dish having a diameter of more than 35 mm, pouring a culture medium onto the dish, and culturing the cells under conditions including a temperature of 36° to 38° C. (normally, 37° C.) and a carbon dioxide concentration of 3% to 10% (normally, 5%). When the cells are observed, the cells are peeled off from the dish and put into the sample capsule.

However, the environment inside the sample capsule is different from the environment on the laboratory dish and so the possibility that cells survive within the specimen container is low. That is, with the sample capsule described in JP-T-2004-515049, only about 15 μl of solution can be put into it. Because the environmental ambients including pH and osmotic pressure vary in a short time, it has been difficult to culture cells.

Examples of a method of acquiring an SEM image by irradiating a specimen with an electron beam via a film capable of withstanding the pressure difference between vacuum and atmospheric pressure in this way and detecting backscattered electrons emanating from the specimen are also described in "Atmospheric scanning electron microscopy," Green, Evan Drake Harriman, Ph.D., Stanford University, 1993 (especially, Chapter 1: Introduction) and JP-A-51-42461.

Examples in which two films of the structure described above are placed opposite to each other with a specimen interposed between the films and in which an image is acquired by a transmission electron microscope are described in JP-A-47-24961 and JP-A-6-318445. Especially, JP-A-47-24961 also states a case in which an SEM image of the specimen interposed between such films is acquired.

A morphological variation caused by a reaction occurring in a cell after a stimulus is given to the cell using a manipulator or pipette takes place in a very tiny region within the cell and, therefore, the variation cannot be observed with an optical microscope. High resolution imaging using SEM is essential. In order to observe cells by SEM while maintaining the liquid, the specimen (cells) cultured on a laboratory dish is sealed into a sample capsule, and then the specimen is irradiated with an electron beam via a film formed on the capsule so as to image the specimen.

However, the sample capsule is a closed space. This makes it impossible to use a manipulator or pipette for giving a stimulus. Furthermore, the probability that cells sealed in sample capsules survive has been low. In addition, even if high resolution imaging is enabled by SEM, it is impossible to identify tissues. It is desired to observe the tissues with an optical microscope simultaneously because the optical microscope permits identification of the tissues.

Consequently, there is a demand for development of a specimen holder which permits cultured cells to be manipulated from the outside or a chemical or medicinal solution to be spread over the cells and which enables a user to well observe and inspect the cells in vivo.

In the above-described specimen holder, it is desired that cells can be cultured for a long time. This enables the specimen to be well observed or inspected in vivo. Additionally, simultaneous observation with an optical microscope and an SEM is preferably enabled such that a stimulus can be given to cultured cells using a manipulator or pipette and that the specimen can be observed or inspected well.

Especially, in a case where a chemical is sprayed over cultured cells using a manipulator or pipette, it is desired to reduce the amount of the sprayed chemical.

SUMMARY OF THE INVENTION

It is an object of the present invention to provide a specimen holder, specimen inspection apparatus, and specimen inspection method which permit the amount of a chemical to be spread over a specimen consisting of cultured cells to be reduced.

A specimen holder, according to one embodiment of the present invention, includes a body portion having a specimen-holding surface and a hole in its bottom. The specimen-holding surface is open to permit access from the outside. The hole is in communication with the specimen-holding surface. The specimen holder further includes a film formed to cover the hole in the body portion. The film has first and second surfaces. The first surface of the film is located on a side of the specimen-holding surface and forms the specimen-holding surface. A concave tapering portion is formed in the specimen-holding surface of the body portion and around the film. A specimen held on the first surface of the film can be irradiated with a primary beam via the film from a side of the second surface of the film to permit observation or inspection of the specimen.

A specimen holder according to another embodiment of the present invention includes a body portion having a specimen-holding surface and a hole in its bottom. The specimen-holding surface is open to permit access from the outside. The hole is in communication with the specimen-holding surface. The specimen holder further includes a film formed to cover the hole in the body portion. The film has first and second surfaces. The first surface of the film is located on a side of the specimen-holding surface and forms the specimen-holding surface. A concave tapering portion is formed in the specimen-holding surface of the body portion and around the film. A specimen held on the first surface of the film can be irradiated with a primary beam via the film from a side of the second surface, which is in contact with a vacuum ambient during the beam irradiation, of the film to permit observation or inspection of the specimen.

A specimen inspection apparatus, according to an embodiment of the present invention, is adapted to observe or inspect a specimen using any one of the above-described forms of the specimen holder, and has holder support means on which the specimen holder is placed, primary beam irradiation means for irradiating the sample placed on the first surface of the film of the specimen holder with a primary beam via the film from a side of the second surface of the film, and signal detection means for detecting a secondary signal produced from the specimen in response to the beam irradiation.

A specimen inspection method, according to one embodiment of the present invention, consists of placing a specimen on the specimen-holding surface of any one of the above-described forms of the specimen holder, irradiating the specimen with a primary beam via the film, and detecting a secondary signal produced from the specimen in response to the beam irradiation.

In the present invention, the specimen cultured on the film located on the open sample holding surface can be irradiated with the primary beam via the film to permit observation or inspection of the specimen.

Consequently, the cultured sample consisting of cells can be well observed or inspected in vivo. Especially, if an electron beam is used as the primary beam, the specimen can be well observed or inspected in vivo by SEM.

Because the specimen-holding surface is open, access (contact or approach) to the specimen is enabled using a pipette or manipulator or a chemical can be spread over the specimen. A stimulus can be given to the specimen using a manipulator. That is, a chemical substance is spread over the specimen or electrical stimulus is given to it. The reaction can be observed or inspected. Additionally, the specimen can be observed with an optical microscope from the opposite side of the primary beam source. The same part of the specimen can be observed almost simultaneously with the SEM and optical microscope.

The surroundings of the film on the specimen-holding surface taper off. The amount of chemical spread over the specimen can be reduced by supplying the chemical only into the interior of the tapering portion using a pipette or manipulator.

Other features and advantages of the present invention will become apparent from the following more detailed description, taken in conjunction with the accompanying drawings, which illustrate, by way of example, the principles of the invention.

DESCRIPTION OF THE PREFERRED EMBODIMENTS

A specimen holder, specimen inspection apparatus, and specimen inspection methods, according to the present invention, are hereinafter described with reference to the drawings.

Embodiment 1

Figure 1:
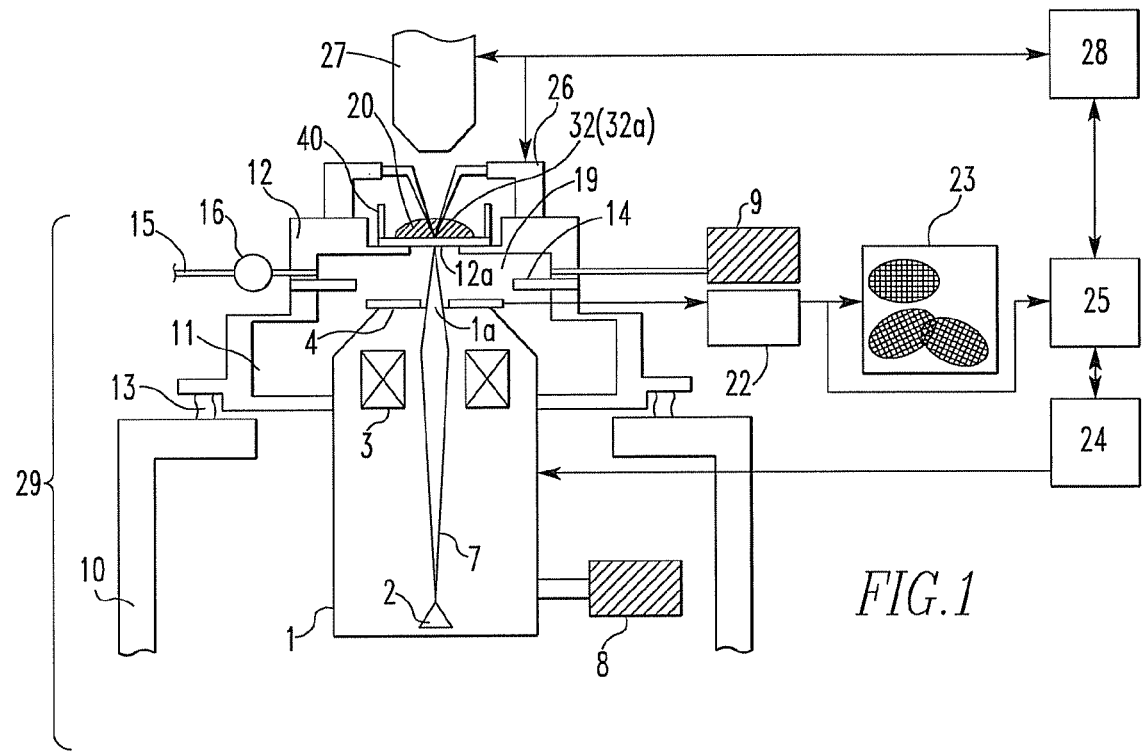
FIG. 1 is a schematic and block diagram of a first embodiment of the specimen inspection apparatus, according to the present invention.

FIG. 1 is a schematic and block diagram of a first embodiment of the specimen inspection apparatus, according to the present invention. The apparatus includes an electron optical column 1 forming the primary beam irradiation system. An electron gun 2 being an electron source is disposed in the electron optical column 1 and emits an accelerated electron beam (or, a charged-particle beam) 7 that is a primary beam. The beam 7 is focused by a condenser lens (objective lens) 3.

The focused electron beam 7 is directed at a sample 20 via a specimen-holding film 32 (described later) formed on a specimen holder 40, the sample 20 being held on the holder 40. The sample 20 includes a specimen (biological cells in the present embodiment) and a liquid (a culture medium in the present embodiment).

During the irradiation, the electron beam 7 is deflected by deflectors (not shown). Thus, the beam 7 scans the sample 20. At this time, the specimen contained in the sample 20 is also scanned with the beam 7.

The front-end side of the electron optical column 1 is connected with a vacuum chamber 11. The electron gun 2 is mounted on the base side of the electron optical column 1, which, in turn, is located below the vacuum chamber 11. Because of this structure, the beam 7 released from the electron gun 2 travels upward through the column 1, passes through an opening 1a formed at the front end of the column 1, goes through the space in the vacuum chamber 11 and through the specimen-holding film 32, and reaches the sample 20.

The electron optical column 1 forms the primary beam irradiation system in this way. In the present embodiment, the column is of the inverted type. A backscattered electron detector 4 is mounted on the front-end side of the optical column 1 inside the vacuum chamber 11. The backscattered electron detector 4 detects backscattered electrons produced when the specimen included in the sample 20 is irradiated with the electron beam 7. For example, a semiconductor detector using a PN junction or a scintillator detector using a YAG crystal is used as the backscattered electron detector 4.

The inside of the electron optical column 1 is pumped down to a desired pressure by vacuum pump 8. The inside of the vacuum chamber 11 is evacuated to a desired pressure by vacuum pump (not shown). The vacuum chamber 11 is placed over a pedestal 10 via a vibration-proofing device 13.

A specimen holder support 12 is mounted on top of the vacuum chamber 11 and provided with a hole 12a to permit passage of the electron beam 7. The specimen holder 40 is placed on the holder support 12 via an O-ring (not shown). Consequently, the specimen holder 40 is withdrawably supported in the vacuum chamber 11.

Figure 2:
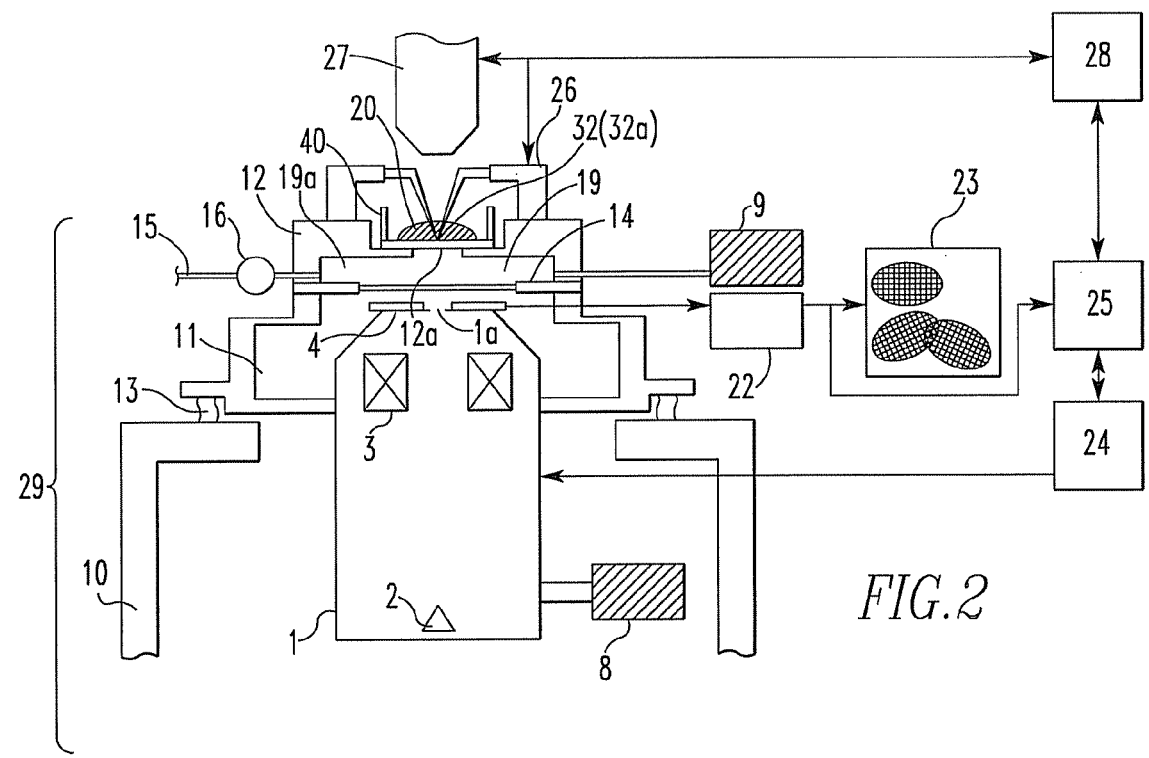
FIG. 2 is a schematic block diagram similar to FIG. 1, but showing a different state.

An open-close valve 14 is mounted at a higher position in the vacuum chamber 11 to partition off a space 19 located between the specimen holder 40 and the front end of the electron optical column (primary beam irradiation system) 1 inside the vacuum chamber 11. FIG. 1 shows the state in which the open-close valve 14 is open. When the open-close valve 14 is closed, the space 19 in the vacuum chamber 11 is partitioned off as shown in FIG. 2. As a result, a hermetically closed space 19a is formed between the open-close valve 14 and the specimen-holding film 32. The closed space 19a is located on the side of the specimen holder 40 as viewed from the open-close valve 14.

Evacuation pump (pressure-reducing means) 9 is mounted in communication with the closed space 19a and can evacuate the closed space 19a independently. A gas supply (not shown) is connected with the closed space 19a. The gas supply supplies a gas, such as nitrogen or air, into the closed space 19a to return the inside of the closed space 19a from a reduced-pressure state to a normal-pressure state (atmosphere). Consequently, the closed space 19a can return from the reduced-pressure state to the normal-pressure state independently.

A cleaning system (not shown) is connected with the closed space 19a. The cleaning system supplies a cleaning agent into the closed space 19a to clean the closed space 19a. As a consequence, the wall surface forming the closed space 19a is cleaned.

The cleaning agent used at this time is a cleaning liquid consisting of at least one of a detergent, ethanol, alcohol, acetone, and aqueous hydrogen peroxide. Alternatively, vapors of these materials may be used. The cleaning agent supplied in the closed space 19a is discharged from it through a discharge tube 15 after the cleaning of the closed space 19a. Another open-close valve 16 is mounted in the discharge tube 15. The open-close valve 16 is opened to permit the cleaning agent to be discharged to the outside through the discharge tube 15. When an inspection (described later) of the specimen is carried out, the valve 16 is closed.

The closed space 19a can be disinfected without using the cleaning agent by irradiating the closed space 19a with ultraviolet radiation or other radiation.

Figure 3:
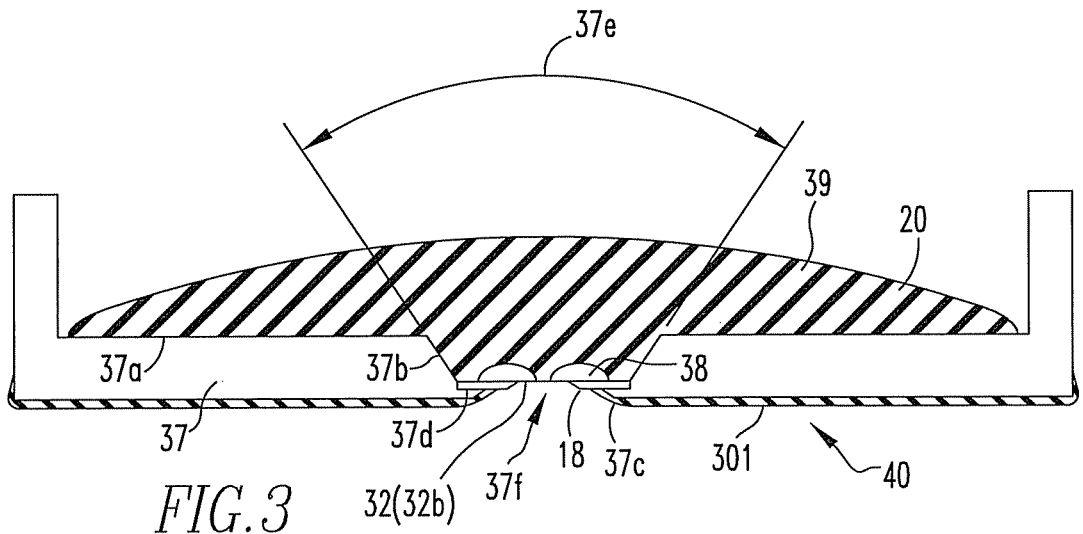
FIG. 3 is a cross-sectional view of a specimen holder, according to the present invention, showing the structure of the holder.

The specimen holder 40 is constructed as shown in FIG. 3. The specimen holder 40 is composed of a dish-like body portion 37 made of plastic or glass and a film holder (frame-like member) 18 on which the specimen-holding film 32 is formed. The film 32 transmits the electron beam 7. A recessed portion is formed inside the dish-like body portion 37. The bottom surface of the recessed portion is composed of a specimen-holding surface 37a and a tapering surface formed on a tapering portion 37b. The inside of the specimen holder 40 is not hermetically closed. The specimen-holding surface 37a and the tapering surface of the tapering portion 37b are open. The difference in height between the specimen-holding surface 37a and the specimen-holding surface of the specimen-holding film 32 is 0.1 to 10 mm. The tapering portion 37b tapers at an angle (37e) of 0° to 170°. If the minimum diameter in the tapering portion 37b is set to 1 to 10 mm, then it is easy to handle the specimen holder.

Another tapering portion 37c is formed on the opposite side of the specimen-holding surface 37a. The tapering portion 37c tapers at an angle of 90° to 120° toward the specimen-holding surface 37a, i.e., spreads away from the specimen-holding surface 37a.

The two tapering portions 37b and 37c are coupled together. The tapering portions 37b and 37c form a hole 37f in the bottom of the body portion 37 of the specimen holder 40. The hole 37f is in communication with the specimen-holding surface 37a of the dish-like body portion 37.

A region of the lower surface of the specimen holder 40 might be exposed to a vacuum ambient and become irradiated with the electron beam 7. A conductive film 301 is formed on this region to prevent charging of the specimen holder 40 when it is irradiated with the beam 7. The conductive film 301 is in contact with the film holder 18. Electric charge accumulated by being irradiated by the electron beam 7 can be dissipated away to the atmosphere via both the film holder 18 made of silicon and the sample 20. The presence of the conductive film 301 reduces the charging of the lower surface of the specimen holder 40 and can prevent displacement of the orbit of the beam 7 (that would normally be produced when the sample 20 is irradiated with the beam 7) and distortion and illumination spots in the SEM image that would be normally produced by displacement of the orbit of backscattered electrons.

Accumulation of electric charge can be prevented effectively by connecting a grounding line to the sample 20 or electrically connecting the conductive film 301 with the specimen holder support 12. The conductive film 301 can be formed, for example, by vapor-depositing aluminum or gold or applying silver paste.

Figure 4A:
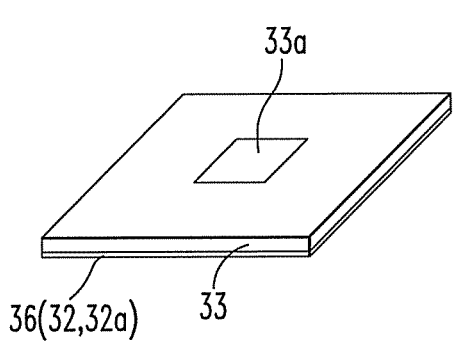
FIGS. 4A and 4B show perspective views illustrating a method of creating a frame-like member constituting the specimen holder, according to the present invention.
Figure 4B:
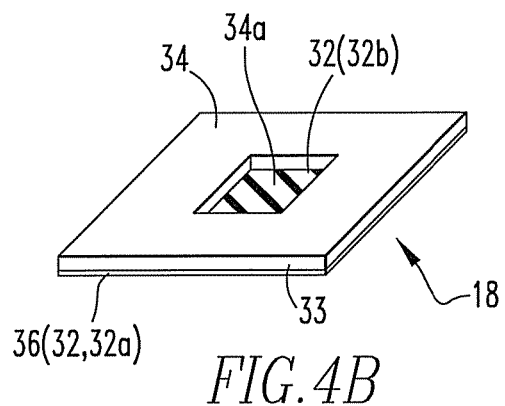

The specimen-holding film 32 is formed on the film holder 18 as shown in FIG. 4B. A first surface 32a of the specimen-holding film 32 (lower surface as viewed in FIG. 4B; upper surface as viewed in FIG. 3) is exposed. The sample 20 containing liquid, such as a culture medium and a specimen (cells), is placed on the first surface (specimen-holding surface) 32a of the specimen-holding film 32. Since the first surface 32a is under atmospheric pressure, evaporation of moisture from the sample 20 can be suppressed to a minimum.

The film holder 18 has a substrate portion 34 formed on the second surface 32b (upper surface in FIG. 4B; lower surface in FIG. 3) of the specimen-holding film 32. The substrate portion 34 is centrally provided with an opening 34a covered with the specimen-holding film 32. A central portion of the second surface 32b of the specimen-holding film 32 is exposed to the inside ambient of the vacuum chamber 11 through the opening 34a.

A method of creating the film holder 18 is next described. First, as shown in FIG. 4A, a substrate having a silicon layer 33 forming the substrate portion 34 and a silicon nitride film 36 formed on one surface (lower surface in FIG. 4A) of the silicon layer 33 is prepared. The silicon nitride film 36 is formed on the silicon layer 33 (substrate portion 34) by a CVD (chemical vapor deposition) technique, such as plasma CVD. The first surface (lower surface in FIG. 4A) of the silicon nitride film 36 is exposed, while the second surface of the silicon nitride film 36 is coated with the silicon layer 33. The silicon nitride film 36 forms the specimen-holding film 32 of the film holder 18.

Then, a central portion 33a of the other (upper) surface of the silicon layer 33 in FIG. 4A is selectively etched. The opening 34a is formed in the central portion 33a of the silicon layer 33 as shown in FIG. 4B. Consequently, a part of the second surface of the silicon nitride film 36 is exposed by the opening 34a, which, in turn, is coated with the silicon nitride film 36. The silicon nitride film 36 forms the specimen-holding film 32 of the film holder 18. The second surface of the silicon nitride film 36 corresponds to the second surface 32b of the specimen-holding film 32. As a result, the film holder 18 made of a frame-like member having the opening 34a is created.

The film holder 18 created in this way is turned upside down from the state of FIG. 4B. The first surface of the silicon nitride film 36 that is the specimen-holding film 32 is taken as an upper surface. The first surface, being the upper surface of the silicon nitride film 36, becomes the first surface 32a of the specimen-holding film 32 of the film holder 18. It is also possible to take the second surface 32b as the upper surface. In FIGS. 4A and 4B, the contour of the film holder 18 is square. According to the need, the film holder may be shaped circularly.

The film holder 18 is firmly held to a bottom surface 37d connected to a lower portion of the tapering portion 37b of the dish-like body portion 37 so as to plug up the hole formed in the dish-like body portion 37. Consequently, the specimen holder 40 is created. To attach the holder 18 to the bottom surface firmly, bonding using a silicone-based or epoxy-based adhesive or fusion making use of heat, ultrasonic waves, or laser light can be used. Furthermore, if cell adhesion molecules (described later) acting as molecules for bonding the specimen are applied to the first surface 32a of the specimen-holding film 32, it is convenient to culture cells.

The thickness of the silicon nitride film 36 is set to a range of from 10 to 1,000 nm. The specimen-holding film 32 of the film holder 18 is made of silicon nitride. In addition, the film 32 may be made of silicon oxide, boron nitride, polymer, polyethylene, polyimide, polypropylene, or carbon. Where films of these materials are used, their film thicknesses are set to a range of from 10 to 1,000 nm. The specimen-holding film 32 made of the aforementioned material transmits the electron beam 7 but does not transmit gas or liquid. Moreover, it is necessary that the film be capable of withstanding a pressure difference of at least 1 atmosphere across the opposite surfaces. As the thickness of the specimen-holding film 32 is reduced, scattering of the electron beam 7 is reduced and, therefore, the resolution is improved but the film is more easily damaged. As the thickness is increased, scattering of the electron beam 7 increases, resulting in decreased resolution. However, the film is less likely to be damaged. The preferable thickness of the film is 20 to 200 nm.

Referring back to FIG. 1, the structure of the specimen inspection apparatus is described in further detail.

A detection signal produced from the backscattered electron detector 4 is fed to an image formation device 22 disposed outside the vacuum chamber 11. The image formation device 22 forms image data based on the detection signal. The image data corresponds to an SEM image.

The image data is sent to a display device 23. An image based on the image data sent in is displayed on the display device 23. The displayed image is an SEM image. Image data created by the image formation device 22 is sent to a computer 25 according to the need. The computer 25 performs image processing on the image data and carries out a decision based on the result of the image processing.

An electron beam apparatus portion 29 equipped with the electron optical column 1 and the vacuum chamber 11 is controlled by an electron beam controller 24. The apparatus portion 29 is located under the specimen holder 40. A manipulator 26 for giving a stimulus (such as a voltage, chemical substance, or medicine) to the specimen and for moving the specimen if necessary and an optical microscope 27 are placed on the specimen holder support 12. The optical microscope 27 permits one to observe the specimen and to check the position of the manipulator 26. These components are controlled by an overall controller 28.

The optical axis of the optical microscope 27 is coincident with the optical axis of the electron beam 7. Alternatively, the center of field of view of the optical microscope 27 is coincident with the center of field of view of the SEM image. A region observed by the optical microscope 27 can be made substantially coincident with the SEM image. The field of view of the SEM image and the field of view of the optical microscope 27 can be adjusted by manipulating the manipulator 26 or moving the specimen holder support 12 on which the specimen holder 40 is installed by means of a moving mechanism (not shown).

The specimen inspection apparatus, according to the present invention, has the electron beam apparatus portion 29, manipulator 26, optical microscope 27, electron beam controller 24, overall controller 28, image formation device 22, and display device 23. These portions are connected with the computer 25. Information can be exchanged between these portions.

An inspection method, according to the present invention, is next described by referring to FIGS. 1, 2, 3, and 5. First, as shown in FIG. 3, cells 38 becoming a specimen are cultured within a culture medium 39 using the specimen holder 40. In order to culture the cells 38 as shown in FIG. 3, it is necessary to graft the cells from the laboratory dish where they have been previously cultured to the specimen holder 40. For this purpose, a normal method as described below is used.

First, the culture medium is discarded from the laboratory dish where the cells have been previously cultured. A mixture liquid of trypsin and EDTA (ethylenediaminetetraacetic acid) is put into the dish to peel off the cells adsorbed to the dish. The peeled cells are recovered into a centrifuge tube. A culture medium is put into the tube. The trypsin is inactivated and then the cells are spun down. Then, the supernatant fluid is discarded from the centrifuge tube and the remaining liquid is stirred in the culture medium. A part (e.g., 1/10) of the stirred liquid including the cells 38 is entered into the specimen holder 40. More culture medium 39 is added. Under this condition, the holder is allowed to stand still in a cell culture chamber. After a lapse of several hours, the cells 38 begin to be adsorbed onto the specimen-holding surface 37a of the specimen holder 40 including the first surface 32a of the specimen-holding film 32 and proliferate.

Figure 5:
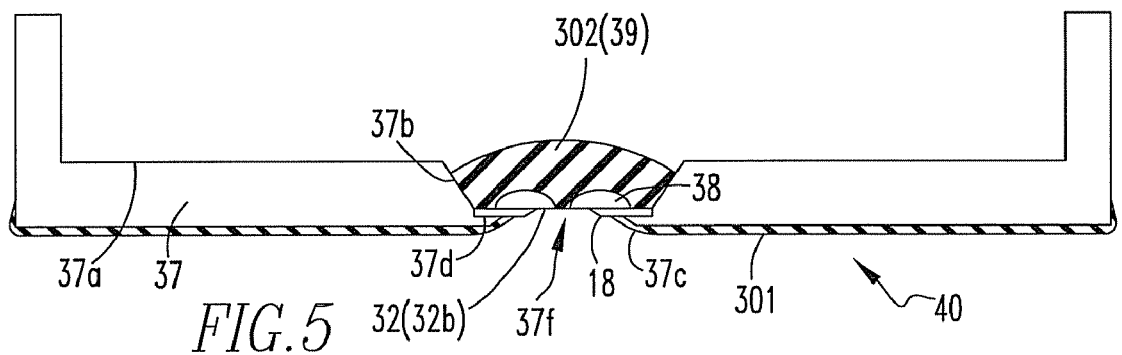
FIG. 5 is a cross section of a specimen holder, according to the present invention, showing the structure of the holder.

As a result, the cells 38 becoming the specimen to be observed or inspected are cultured within the specimen holder 40. The sample 20 including the cultured cells 38 and culture medium 39 is constituted. Where the cells cultured in the specimen holder 40 are small in amount, the culture medium 39 including the cells 38 may be put into only the tapering portion 37b as shown in FIG. 5. Then, at the instant when the cells 38 are adsorbed onto the specimen-holding film 32, the culture medium 39 is added to realize the state shown in FIG. 3. This enables long-term cultivation.

Depending on biological cells, if cell adhesion molecules are applied to the specimen-holding surface 37a of the specimen holder 40 (especially, the first surface (specimen-holding surface) 32a of the specimen-holding film 32 observed with an electron beam), cultivation is facilitated. The cell adhesion molecules cause cells arranged for cultivation and cells proliferated by cultivation to be adsorbed onto the sample-holding surface. Examples of the cell adhesion molecules include collagen, fibronectin, vitronetin, cadherin, integrin, claudins, desmogleins, neuroligin, neurexin, selectin, laminins, and poly-L-lysine. By causing the cells to adhere to the specimen-holding film 32 via the cell adhesion molecules as described above, deterioration of the resolution due to scattering of the electron beam 7 can be reduced to a minimum when the cells are irradiated with the beam 7 via the specimen-holding film 32.

After the cells becoming a specimen are cultured within the specimen holder 40 as described above, the specimen holder 40 is placed on the holder support 12. At this time, the open-close valve 14 is closed and in the state of FIG. 2. The closed space 19a hermetically sealed between the valve 14 and the specimen-holding film 32 is at a normal pressure or in an atmospheric-pressure ambient. Within the vacuum chamber 11, the space located under the valve 14 is in a given vacuum state (reduced-pressure state).

The inside of the electron optical column 1 in communication with this space is evacuated to a desired vacuum state by the vacuum pump 8. The pressure (degree of vacuum) inside the vacuum chamber 11 is set to about $10^{-1}$ to $10^{-4}$ Pa, for example. The pressure (degree of vacuum) inside the electron optical column 1 (especially, around the electron gun 2) is set to about $10^{-4}$ to $10^{-5}$ Pa, for example.

Under this condition, the closed space 19a is reduced in pressure down to a vacuum using the evacuation pump 9. At this time, to prevent the specimen-holding film 32 from being damaged due to rapid pressure variations from the atmospheric-pressure state, the pressure is reduced from 1 atm. (101325 Pa), that is, the atmospheric pressure down to about ½ to 1/10 atm. (50 kPa to 10 kPa), using a needle valve (not shown), in a time from 1 second to 100 seconds. During this process step, it is checked that the specimen-holding film 32 of the specimen holder 40 is not destroyed.

After checking that the specimen-holding film 32 has not been destroyed by the above-described step, the positions of the cells (specimen) 38 and of the manipulator 26 are checked with the optical microscope 27. Microelectrodes and a glass microtube are installed at the front end of the manipulator 26. A voltage can be applied to the cells through the microelectrodes. A liquid can be made to flow in and out through the glass microtube.

Under this condition, the manipulator 26 is moved while making an observation with the optical microscope 27 to bring the cells 38 close to the glass microtube. Then, a negative pressure is applied to the glass microtube to bring it into intimate contact with the cell membranes. As a result, potential response can be measured.

When the manipulator 26 is moved as described above, if the specimen-holding film 32 is erroneously damaged, contamination due to diffusion of the sample 20 is restricted to within the closed space 19a because the open-close valve 14 is closed. If the specimen-holding film 32 should be damaged and the inside of the closed space 19a be contaminated due to diffusion of the sample 20, cleaning of the closed space 19a is possible as described previously.

The liquid detergent or vapor used for the cleaning can be discharged and discarded via the discharge tube 15 by opening the open-close valve 16. It is possible to make the closed space 19a less susceptible to contamination by coating the wall surface forming the closed space 19a with boron nitride or fluororesin.

When the closed space 19a is in a reduced-pressure state or a vacuum state, it is checked that the specimen-holding film 32 on which the sample 20 is placed is not destroyed. Then, the open-close valve 14 is opened. Thus, the space inside the vacuum chamber 11 is ceased to be partitioned to place the space located under the vacuum chamber 11 into communication with the closed space 19a. Thereafter, in order to prevent light from entering the backscattered electron detector 4 via the specimen-holding film 32, the light irradiation of the optical microscope 27 is ceased. Other extraneous light is blocked in a manner not shown. The blocking also shields the film holder 18 and sample 20 against radiation rays produced when the electron beam 7 hits the film holder 18 and sample 20.

Then, as shown in FIG. 1, the electron beam 7 is directed at the sample 20 including the cells 38 from the electron optical column 1 to perform imaging. The beam 7 passes through the specimen-holding film 32 of the specimen holder 40 and hits the cells 38. Backscattered electrons produced from the cells 38 in response to the irradiation are detected by the backscattered electron detector 4.

Since the aforementioned tapering portion 37c is formed in the hole 37f of the dish-like body portion 37 forming the specimen holder 40, collision of the backscattered electrons against the inner side surface of the tapering portion 37c can be suppressed to a minimum. That is, the backscattered electrons can be suppressed from being blocked. The backscattered electrons can be detected efficiently by the backscattered electron detector 4.

A detection signal produced from the backscattered electron detector 4 is fed to the image formation device 22, which, in turn, forms image data based on the detection signal. Based on the image data, an image (SEM image) is displayed on the display device 23.

Subsequently, an electrical stimulus is given to the cells 38 using the microelectrodes installed at the front end of the manipulator 26. An SEM image is acquired in the same way as in the above-described process step. The response of the cells 38 to the stimulus is checked.

After the imaging, the open-close valve 14 is closed to prevent contamination of the electron optical column 1 if the specimen-holding film 32 should be destroyed. Before a variation caused by application of a stimulus to the cells 38 is observed by SEM as described above, an observation may be made with the optical microscope 27. Also, at this time, if the open-close valve 14 is closed, risk of contamination occurring when the specimen-holding film 32 is broken can be reduced. In any case, if the open-close valve 14 is closed when the electron beam 7 is not directed at the sample 20, the probability of contamination of the inside of the apparatus can be reduced by shortening the interval for which the open-close valve 14 is opened during inspection.

Where the speed of reaction of the cells 38 to the stimulus is low, the open-close valve 14 may be once closed. The valve 14 may be again opened at a time when a reaction is deemed to have taken place. Then, imaging may be performed using the electron beam 7. The reaction can be checked with the optical microscope 27.

The manipulator 26 can have a mechanism capable of spraying a chemical substance or medicine into the sample 20. Behavior of the cells 38 in response to the chemical substance or medicine can be observed or inspected while observing the cells by SEM. When a chemical substance is sprayed in this way, if the chemical substance is expensive or small in amount, the chemical substance 302 can be easily given to cells because the tapering portion 37b has been machined in the specimen holder 40 provided that the amount of the chemical substance 302 is small as shown in FIG. 5. This method is effective in a case where a chemical substance is sprayed over cells using a pipette instead of a manipulator.

Where the chemical substance is recovered using a pipette, it is necessary to bring it close to the specimen-holding surface 32a of the specimen-holding film 32. In this case, however, the central portion of the specimen-holding surface 32a that is exposed by the opening 34a in the substrate portion 34 forming the film holder (frame-like member) 18 is only 10 to 1,000 mm thick and, therefore, there is the danger that the central portion is destroyed by the pipette.

To solve this problem, a step portion 61a is formed on the body portion 37 and a pipette contact surface 61 is formed on the underside of the step portion 61a to permit the pipette 62 to be brought close to the first specimen-holding surface 32a. Preferably, the pipette contact surface 61 is located substantially flush with the specimen-holding surface 32a of the specimen-holding film 32.

Figure 7:
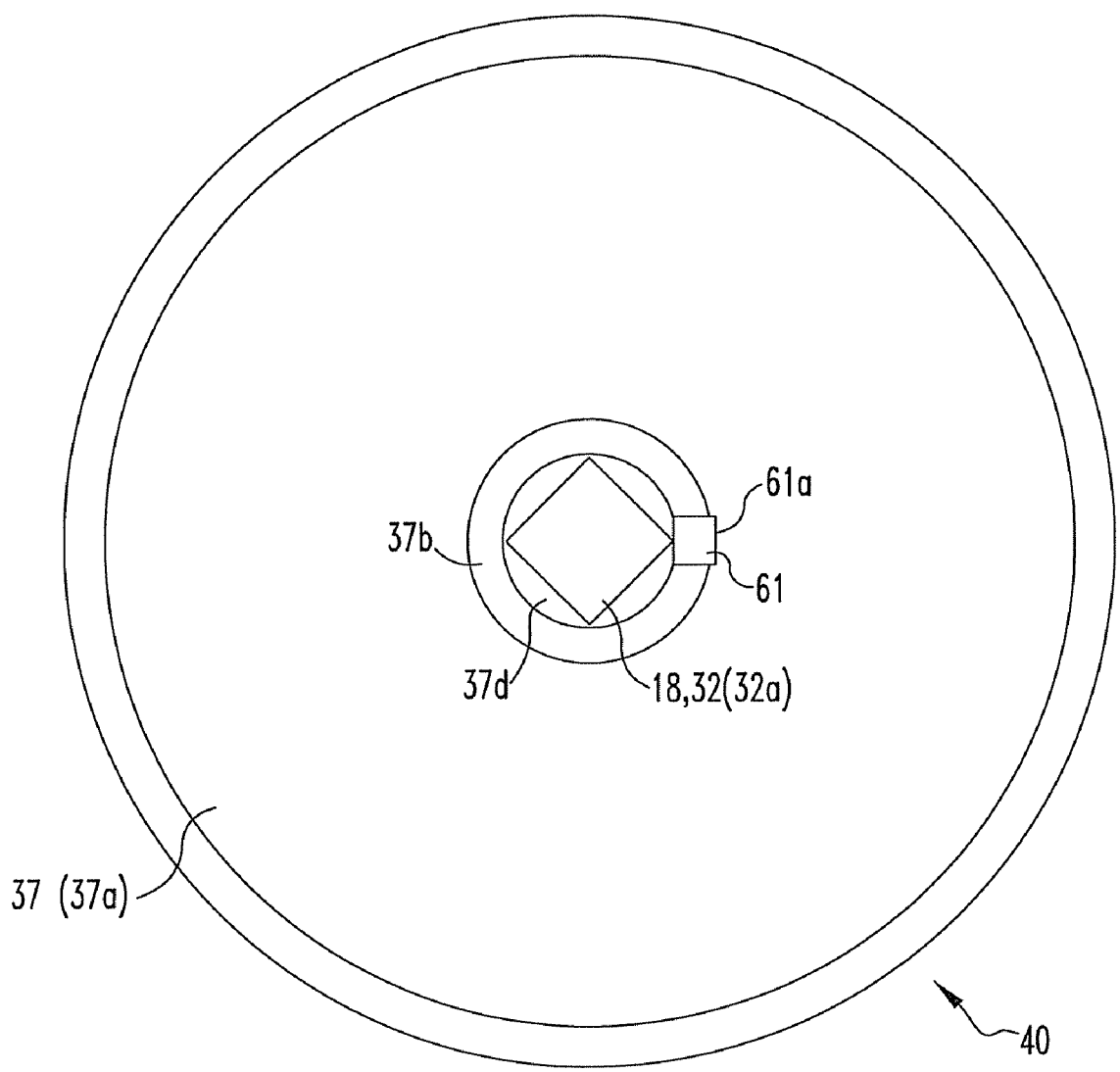
FIG. 7 is a top plan view of the specimen holder shown in FIG. 6, showing the structure of the holder.

Consequently, the first specimen-holding surface 32a of the specimen-holding film 32 can be placed in communication with the bottom surface 37d (pipette contact surface 61) of the step portion 61a. The chemical substance inside the tapering portion 37b can be recovered with certainty through the front end of a pipette 62 positioned on the pipette contact surface 61. FIG. 7 shows the state in which the specimen holder 40 on which the step portion 61a is formed is viewed from above.

Figure 6:
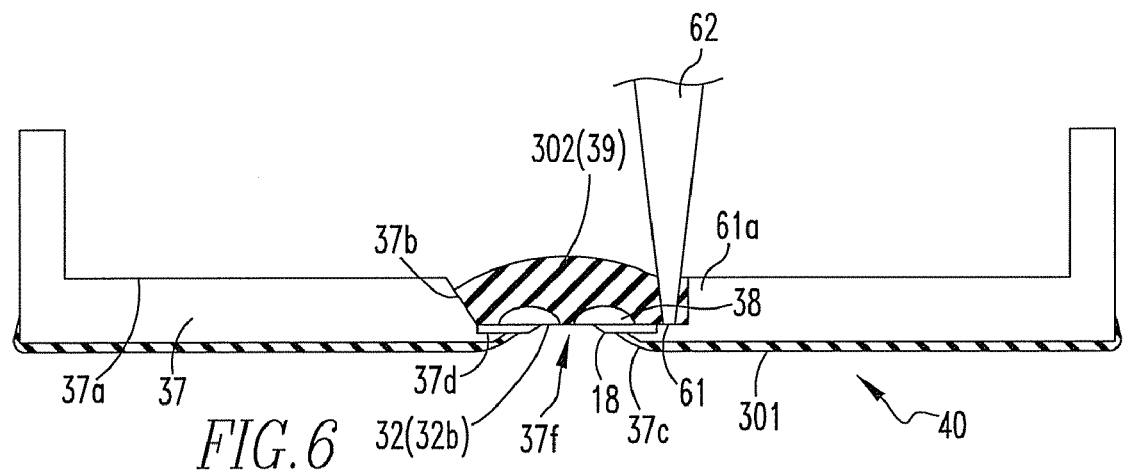
FIG. 6 is a cross section of another specimen holder, according to the present invention, showing the structure of the holder.

Furthermore, a function of permitting a liquid to flow out can be imparted to the manipulator 26. This permits the sprayed chemical substance to be recovered. Also, the pH of the culture medium and the osmotic pressure can be maintained constant. In this case, the manipulator 26 can be used instead of the pipette 62 shown in FIG. 6.

In the foregoing, backscattered electrons are used to form an image. Backscattered electrons produce a signal intensity proportional to the atomic number. Therefore, where the specimen is almost totally made of substances of low atomic numbers, such as a biological specimen, the image contrast is very low, and it is difficult to improve the resolution.

Accordingly, a heavy metal, such as gold, may be adsorbed onto portions of the cells 38 to be noticed in their behavior. In particular, gold is adsorbed onto the portions (antigen) via an antibody by causing the antigen tagged with gold particles having the nature of being adsorbed on the portions (antigen) to be sprayed over the cells by making use of an antigen-antibody reaction. Furthermore, a fluorescent dye or quantum dots (e.g., nanoparticles of Si or particles of CdSe coated with ZnS and having sizes of 10 to 20 nm) that emit light when irradiated with an electron beam may be previously adsorbed onto certain portions of the cells 38, and the emitted light may be observed with an optical microscope.

These chemical substances are generally expensive and so it is desired to reduce the amount of the used chemical substance to a minimum. This requirement can be effectively attained by using the specimen holder 40 of the present invention. As shown in FIG. 5, a chemical substance 302 is held only on the tapering portion 37b. This can reduce the amount of the used chemical substance 302. After placing the chemical substance 302 on the tapering portion 37b, the substance is washed away. Then, the amount of the culture medium 39 is increased as shown in FIG. 3 to facilitate cultivation of cells.

In the above embodiment, normally used gold particles have particle diameters of 10 to 30 nm. However, the adsorptive force between the antibody and gold particles is weak, gold particles of 10 to 30 nm may not be attached. In this case, very small gold particles (nanogold particles) having particle diameters on the order of nanometers are first attached to the antibody. Under this condition, the gold particles are too small and it is difficult to observe them by SEM. Silver is adsorbed around the gold particles by making use of a silver sensitizer. This makes it easier to detect them by SEM.

Embodiment 2

An example is described in which the same portion of a specimen is observed almost simultaneously with an optical microscope and an SEM. Biological cells are cultured with the specimen holder 40 by the method described in embodiment 1 as shown in FIG. 3. Then, the cells are fixed using glutaraldehyde or formaldehyde.

Furthermore, the cells are stained to facilitate observation with the optical microscope and SEM. First, the tissues of the cells are stained separately for optical microscopy. For example, in order to stain cellules, the SelectFX Alexa Fluor 488 Endoplasmic Reticulum Labeling Kit available from Invitrogen Corporation may be used. Subsequently, phosphotungstic acid is used for SEM to stain the proteins of the cells. The efficiency at which backscattered electrons are released is enhanced. If these chemicals are expensive, chemical substance 302 can be supplied only into the tapering portion 37b to reduce the amount of the used chemical substance 302.

After completing the pretreatment in this way, the specimen holder 40 is placed on the specimen holder support 12 as shown in FIG. 1 and an observation is made in the same way as in embodiment 1. Because the upper side of the specimen holder 40 is open, it is possible to make an observation with the optical microscope 27 while making an SEM observation. Furthermore, the optical microscope 27 and SEM observations of the same portion of a specimen can be made almost simultaneously because the optical axis of the optical microscope 27 is coincident with the optical axis of the electron optical column 1. Consequently, the position of the tissues of interest (e.g., cellules) can be determined with the optical microscope, and a high-resolution SEM image can be obtained.

In the foregoing embodiment, cells previously cultured in a laboratory dish are taken out and grafted onto the specimen holder 40, where the cells are cultured. Alternatively, cells may be taken as another specimen from a living organism, directly placed on the first specimen-holding surface 32a of the specimen holder 40, and cultured.

In the embodiment described so far, the open specimen holder 40 is used and so reactions of cells to a stimulus can be imaged and inspected in vivo at high resolution by SEM, which has been heretofore impossible to achieve. Furthermore, the specimen holder is made usable that enables inspection of cells by the specimen inspection apparatus while the cells are being cultured. In addition, the same portions of cells can be observed substantially simultaneously with an optical microscope and an SEM, whether the cells are dead or alive. A high-resolution image can be derived by SEM. The tissues of the cells can be stained separately with the optical microscope. The tissues in the high-resolution image can be identified. Additionally, observations under liquid environments are possible. This dispenses with the prior-art steps for observations under vacuum environments including dehydration, drying, and metal vapor deposition. The pretreatment can be carried out at a higher speed. High throughput observations can be achieved.

The cells referred to in the above embodiments are various tissue cells including adrenal cortical cells, cardiac muscle cells, gastric cells, intestinal cells, and vascular cells.

In the above embodiments, backscattered electrons are used as a secondary signal. Information about the specimen 38 consisting of cells can also be obtained by detecting secondary electrons, X-rays, or cathodoluminescent light produced when the specimen 38 is irradiated with the electron beam 7 or electric current absorbed into the specimen 38. It is convenient to use the manipulator 26 in measuring the absorption current.

It is required that the specimen-holding film 32 of the present embodiment withstands a pressure difference of at least 1 atm. and that gas or liquid do not flow in or out. Specifically, the material of the film 32 includes at least one of polymer, polyethylene, polyimide, polypropylene, carbon, silicon oxide, silicon nitride, and boron nitride.

In the above embodiments, an electron beam is used as the primary beam. If the specimen-holding film 32 shows sufficient shock resistance and strength against impingement of other charged-particle beams, such as a helium ion beam, the invention can also be applied in a case where the another charged-particle beam is used. In addition, an inverted SEM is used in the above embodiments. Depending on the specimen, a normal, non-inverted SEM may be used without problem.

In this way, the specimen holder 40 of the present invention has the dish-like body portion 37 provided with the specimen-holding surface 37a and the hole 37f in its bottom and the film 32 whose first surface forms the first specimen-holding surface 32a. The specimen-holding surface 37a is made open to permit access from the outside. The hole 37f is in communication with the specimen-holding surface 37a. The film is disposed to cover the hole 37f in the dish-like body portion 37. The first surface of the film 32 is located on a side of the specimen-holding surface 37a. The concave tapering portion 37b is formed in the specimen-holding surface 37a of the dish-like body portion 37 and around the film 32. The sample 20 including the specimen 38 held on the first surface of the film 32 can be irradiated with a primary beam for observation or inspection of the specimen from a side of the second surface 32b of the film 32 via the film 32.

Especially, the sample 20 held on the first surface 32a of the film 32 can be irradiated with a primary beam for observation or inspection of the specimen via the film 32 from a side of the second surface 32b of the film 32 in contact with a vacuum environment. The film 32 is formed on the film holder (frame-like member) 18 and covers the opening 34a in the film holder (frame-like member) 18. The film holder (frame-like member) 18 is located in a corresponding manner to the hole 37f in the dish-like body portion 37.

Preferably, the tapering portion 37b formed in the dish-like body portion 37 tapers at an angle (37e) of 0 to 170 degrees.

Preferably, the tapering portion 37b formed in the dish-like body portion 37 is shaped like a truncated cone. The inside minimum diameter is between 1 mm and 10 mm.

Preferably, in the tapering portion 37b formed in the dish-like body portion 37, the height from the first surface 32a of the film 32 to the upper surface of the tapering portion 37b is between 0.1 mm and 10 mm.

The step portion 61a which is adjacent to the film 32 and has its bottom surface 37d in communication with the first surface 32a of the film 32 can be formed on the dish-like body portion 37. A chemical supplied into the tapering portion 37b can be recovered efficiently without damaging the film 32 by placing the front end of the pipette 62 on the bottom surface 37d of the step portion 61a.

In the above-described various forms of the specimen holder 40, the specimen included in the sample 20 (such as cells, tissues, viruses, or germs) can be cultured at least on the first surface 32a of the film 32.

The thickness of the film 32 can be set to a range of from 10 nm to 1,000 nm. More preferably, the thickness of the film 32 can be set to between 20 nm and 200 nm.

The primary beam 7 directed at the specimen via the film 32 of the specimen holder 40 can be an electron beam or an ion beam.

A specimen inspection apparatus of the present invention is used to observe or inspect a specimen using any one of the above-described various forms of the specimen holder 40. The specimen inspection apparatus has the specimen holder support 12 on which the specimen holder 40 is placed, the primary beam irradiation means 1 for irradiating the specimen 38 placed on the first surface 32a of the film 32 of the specimen holder 40 with the primary beam 7 via the film 32 from a side of the second surface 32b of the film 32, and the signal detector 4 for detecting a secondary signal produced from the specimen 38 in response to the irradiation by the primary beam 7.

The vacuum chamber 11 is installed in the specimen inspection apparatus to make the ambient in contact with the second surface 32b of the film 32 of the specimen holder 40 a vacuum ambient.

The first surface 32a of the film 32 is the upper surface of the film 32. The second surface 32b of the film 32 is the lower surface of the film 32.

Furthermore, there is provided the optical microscope 27 for acquiring an optical image of the specimen 38 held on the first surface 32a of the film 32 of the specimen holder 40.

A specimen inspection method of the present invention consists of disposing the specimen 38 on the specimen-holding surface 37a of any one of the above-described forms of the specimen holder 40, irradiating the specimen 38 with the primary beam 7 via the film 32, and detecting a secondary signal produced from the specimen 38 in response to the irradiation by the beam 7.

During the irradiation by the primary beam 7, the second surface 32b of the film 32 of the specimen holder 40 is in contact with a vacuum ambient. The primary beam 7 is directed at the specimen through the vacuum ambient.

The primary beam 7 is an electron beam or ion beam. The secondary signal is any one type of secondary electrons, backscattered electrons, absorption current, cathodoluminescent light, and X-rays.

In the present invention, the specimen 38 cultured on the film 32 located on the open specimen-holding surface 37a can be irradiated via the film 32 with the primary beam 7 for observation or inspection of the specimen.

Consequently, the specimen 38, such as biological cells, can be well observed or inspected in vivo while the specimen is being cultured. Especially, if an electron beam is used as the primary beam 7, the specimen 32 can be well observed or inspected in vivo by SEM.

Because the specimen-holding surface 37a is open, access (contact or approach) to the specimen 38 using the pipette 62 or manipulator 26 is allowed. Also, a chemical can be sprayed over the specimen 38. A stimulus, such as spraying of a chemical substance or electrical stimulus, can be given to the specimen using the manipulator 26. The resulting reaction can be observed or inspected. Furthermore, the specimen can be observed with the optical microscope from the opposite side of the primary beam source. The same portion of the specimen can be observed almost simultaneously with the two instruments.

Especially, the film 32 of the specimen-holding surface 37a has the tapering peripheral portion. The amount of the sprayed chemical (i.e., the amount of the used chemical) can be reduced by supplying the chemical only into the tapering portion 37c using the pipette 62 or manipulator 26.

Having thus described our invention with the detail and particularity required by the Patent Laws, what is desired protected by Letters Patent is set forth in the following claims.

The invention claimed is:

1. A specimen holder comprising:
a body portion having a specimen-holding surface and a hole in its bottom, the specimen-holding surface being made open to permit access from the outside, the hole being in communication with the specimen-holding surface;
a film disposed to cover the hole in the body portion and having a first surface located on a side of the specimen-holding surface, the first surface forming the specimen-holding surface; and
a concave tapering portion formed in the specimen-holding surface of the body portion and around the film,
wherein a primary beam for observation or inspection of the specimen can be directed at the specimen via the film from a side of a second surface of the film when the specimen is held on the first surface of the film.

2. A specimen holder comprising:
a body portion having a specimen-holding surface and a hole in its bottom, the specimen-holding surface being made open to permit access from the outside, the hole being in communication with the specimen-holding surface;
a film disposed to cover the hole in the body portion and having a first surface located on a side of the specimen-holding surface, the first surface forming the specimen-holding surface; and
a concave tapering portion formed in the specimen-holding surface of the body portion and around the film,
wherein a primary beam for observation or inspection of the specimen can be directed at the specimen via the film from a side of the second surface, which is in contact with a vacuum ambient during the beam direction, of the film when the specimen is held on the first surface of the film.

3. A specimen holder as set forth in claim 1 or 2, wherein said film is formed on a frame-like member and covers an opening in the frame-like member, and wherein the frame-like member is disposed in a corresponding manner to the hole in the body portion.

4. A specimen holder as set forth in claim 1 or 2, wherein said tapering portion formed in the body portion tapers at an angle of 0 to 170 degrees.

5. A specimen holder as set forth in claim 1 or 2, wherein the tapering portion formed in the body portion is shaped like a truncated cone and has an inside minimum diameter of 1 to 10 mm.

6. A specimen holder as set forth in claim 1 or 2, wherein the tapering portion formed in the body portion has a height of 0.1 to 10 mm as measured from the first surface of said film to an upper surface of the tapering portion.

7. A specimen holder as set forth in claim 1 or 2, wherein said body portion has a step portion which is adjacent to said film and which has a surface in communication with the first surface of the film.

8. A specimen holder as set forth in claim 1 or 2, wherein cells, tissues, viruses, or germs contained in the specimen can be cultured on at least the first surface of said film.

9. A specimen holder as set forth in claim 1 or 2, wherein said film has a thickness of 10 to 1,000 nm.

10. A specimen holder as set forth in claim 1 or 2, wherein said film has a thickness of 20 to 200 nm.

11. A specimen holder as set forth in claim 1 or 2, wherein said primary beam is an electron beam or an ion beam.

12. A specimen inspection apparatus for observing or inspecting a specimen using a specimen holder as set forth in claim 1 or 2, said specimen inspection apparatus comprising:
support means on which the specimen holder is placed;
primary beam irradiation means for irradiating the specimen placed on the first surface of the film of the specimen holder with a primary beam via the film from a side of the second surface of the film; and
signal detection means for detecting a secondary signal produced from the specimen in response to the irradiation by the primary beam.

13. A specimen inspection apparatus as set forth in claim 12, further comprising a vacuum chamber for making the ambient in contact with the second surface of the film of the specimen holder a vacuum ambient.

14. A specimen inspection apparatus as set forth in claim 12, wherein said primary beam is an electron beam or an ion beam, and wherein said secondary signal is one type of secondary electrons, backscattered electrons, absorption current, cathodoluminescent light, and X-rays.

15. A specimen inspection apparatus as set forth in claim 12, wherein the first surface of said film is an upper surface of the film, while the second surface of the film is a lower surface of the film.

16. A specimen inspection apparatus as set forth in claim 12, further comprising optical image acquisition means for acquiring an optical image of the specimen held on the first surface of the film of said specimen holder.

17. A specimen inspection method comprising the steps of:
preparing a specimen holder as set forth in claim 1;
placing a specimen on the specimen-holding surface of the specimen holder;
irradiating the specimen with a primary beam via the film; and
detecting a secondary signal emanating from the specimen in response to the beam irradiation.

18. A specimen inspection method as set forth in claim 17, wherein during the irradiation by the primary beam, the second surface of the film of said specimen holder is in contact with a vacuum ambient and the primary beam is directed at the specimen through the vacuum ambient.

19. A specimen inspection method as set forth in claim 17, wherein said primary beam is an electron beam or an ion beam, and wherein said secondary signal is one type of secondary electrons, backscattered electrons, absorption current, cathodoluminescent light, and X-rays.

* * * * *